US00PP26028P2

(12) United States Plant Patent
Probst

(10) Patent No.: US PP26,028 P2
(45) Date of Patent: Oct. 27, 2015

(54) ***ASTILBE* PLANT NAMED 'AMBER MOON'**

(50) Latin Name: ***Astilbe* hybrid**
Varietal Denomination: Amber Moon

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 91 days.

(21) Appl. No.: 13/999,410

(22) Filed: Feb. 24, 2014

(51) Int. Cl.
*A01H 5/02* (2006.01)

(52) U.S. Cl.
USPC ..... Plt./407

(58) Field of Classification Search
USPC ..... Plt./407
See application file for complete search history.

*Primary Examiner* — Susan McCormick Ewoldt
(74) *Attorney, Agent, or Firm* — Penny J. Aguirre

(57) ABSTRACT

A new cultivar of *Astilbe* named 'Amber Moon' that is characterized by its foliage when grown in bright shade that emerges orange-yellow in color, changing to yellow when fully expanded, and finally changing to yellow-green with a whitish silver blush after flowering, its flowers that are pink in color, and its very high heat tolerance in comparison to most cultivars of *Astilbe*.

2 Drawing Sheets

Botanical classification: *Astilbe* hybrid.
Varietal denomination: 'Amber Moon'.

BACKGROUND OF THE INVENTION

The present invention relates to a new and distinct cultivar of *Astilbe* of hybrid origin and will be referred to hereafter by its cultivar name, 'Amber Moon'. 'Amber Moon' represents a new *Astilbe*, an herbaceous perennial grown for landscape use.

The Inventor discovered a naturally occuring leaf mutation on an unlabled *Astilbe* hybrid in a trial garden in Hubbardston, Mass. in spring of 1989. Based on the characteristics, the parent plant it is thought to be *Astilbe* 'Cattleya' (not patented). A single gold leaf was observed on a compound leaf and after several generations of rhizome division, the new cultivar, Amber Moon', with gold foliage throughout the plant was selected.

Asexual propagation of the new cultivar was first accomplished by the Inventor by rhizome division in Hubbardston, Mass. in 1994. Asexual propagation by tissue culture and rhizome division has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Amber Moon' as a unique cultivar of *Astilbe*.

1. 'Amber Moon' exhibits foliage when grown in bright shade that emerges orange-yellow in color, changing to yellow when fully expanded, and finally changing to yellow-green with a whitish silver blush after flowering.
2. 'Amber Moon' exhibits flowers that are pink in color.
3. 'Amber Moon' exhibits very high heat tolerance in comparison to most cultivars of *Astilbe*.

The probable parent of 'Amber Moon', 'Cattleya', is similar to 'Amber Moon' in having a similar plant height, in having similarly shaped pyramidal panicles, and in having flowers that are pink in color. 'Cattleya' differs from 'Amber Moon' in having foliage that is solid green in color. 'Amber Moon' can be most closely compared to the *Astilbe* cultivars, 'Beauty of Lisse' (U.S. Plant Pat. No. 17,816) and 'Hip Hop' (U.S. Plant Pat. No. 24,165). 'Beauty of Lisse' is similar to 'Amber Moon' in having foliage that is yellow in color. 'Beauty of Lisse' differs from 'Amber Moon' in having foliage that is only transiently yellow and changes to a green color in the heat of summer, in having flowers that are light red-purple in color, and in being less cold hardy and less heat tolerant. 'Hip Hop' is similar to 'Amber Moon' in being heat tolerant. 'Hip Hop' differs from 'Amber Moon' in having foliage that is green in color and in having very densely branched foliage that grows closer to the inflorescences.

BRIEF DESCRIPTION OF THE DRAWINGS

The accompanying colored photographs illustrate the overall appearance and distinct characteristics of the new *Astilbe*. The photographs were taken of 4 year-old plants as grown outdoors in the ground in Zeeland, Mich.

The photograph in FIG. 1 provides a close-up view of the spring foliage of 'Amber Moon'.

Figure 1:
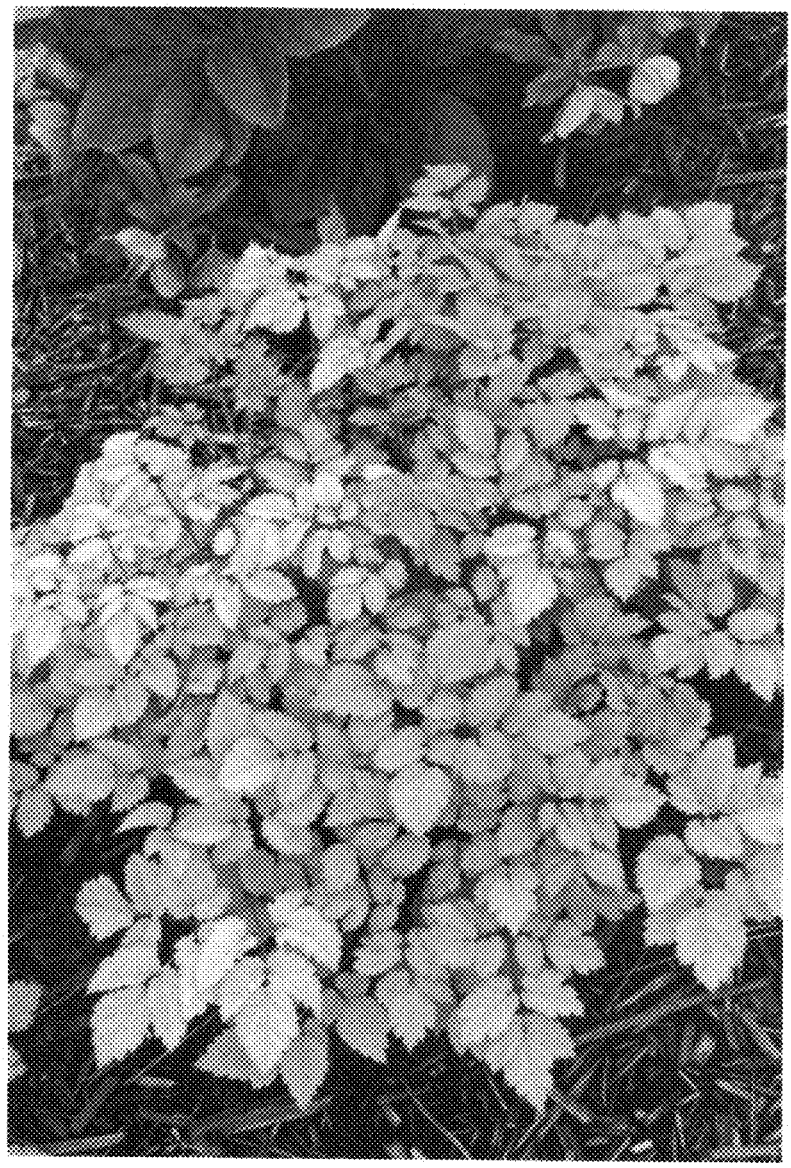
Figure 2:
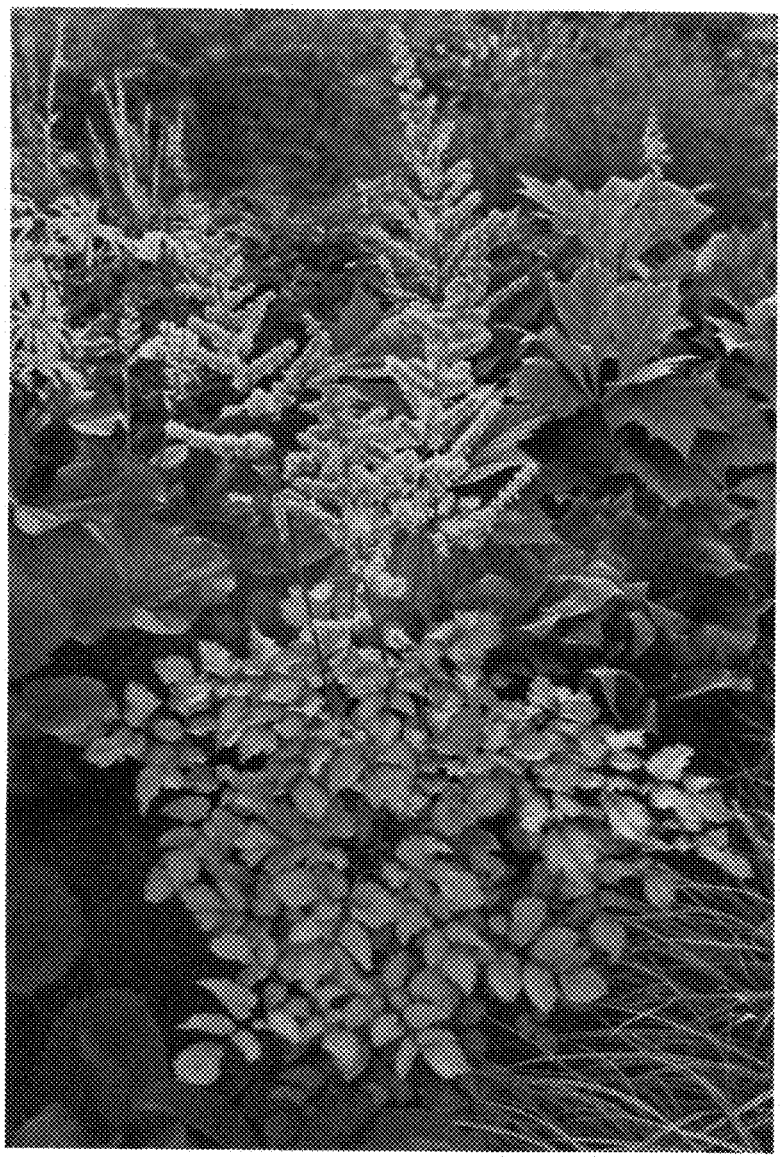

The photograph in FIG. 2 provides a side view of 'Amber Moon' in bloom.

The colors in the photographs are as close as possible with the digital photography and printing techniques utilized and the color codes in the detailed botanical description accurately describe the colors of the new *Astilbe*.

DETAILED BOTANICAL DESCRIPTION

The following is a detailed description of 4 year-old plants of the new cultivar as grown in the ground in Zeeland, Mich. with heat tolerance observed on plants grown in a trial garden in Raleigh, N.C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Three to four weeks in early summer.

*Plant type.*—Herbaceous perennial.

*Plant habit.*—Clump-forming, a spreading mound of foliage with upright bloom stalks with inflorescences that are held above the foliage.

*Height and spread.*—Reaches 60 to 76 cm in height and 45 to 60 cm in spread.

*Hardiness.*—At least in U. S. D. A. Zones 3 to 8.

*Diseases and pests.*—No resistance or suseptibility to diseases and pests has been observed.

*Environmental conditions.*—Observed to be highly heat tolerant in the summer heat in Raleigh, N.C.

*Propagation.*—Rhizome division and tissue culture.

*Growth rate.*—Moderate to vigorous.

Stem description:

*Stem color.*—Young; base is a blend of 183A and 158A, becoming a blend of 183A and 144A, mature; blend of 146A and 200B.

*Stem shape.*—Round.

*Stem size.*—Up to 76 cm in length (including peduncle) and up to 5 mm in diameter.

*Stem quantity.*—Average of 33 main stems.

*Stem surface.*—Moderately glossy, bases of stems moderately covered with short hairs, average of 2 mm in length and ranges between NN155A and 165A in color.

*Stem aspect.*—Very strong, mostly held upright.

*Branching habit.*—No lateral branches, stems grow from the base.

*Nodes.*—Color is 183A with edged color of 140A, up to 8 mm in diameter.

Foliage description:

*Leaf division.*—Compound.

*Leaf attachment.*—Petiolate.

*Leaf arrangement.*—Opposite.

*Leaf shape.*—Cordate.

*Leaf number.*—Average of 8 per stem.

*Internode length.*—Average of 12 cm.

*Leaf size.*—Average of 5.5 cm in length and 16.1 cm in width.

*Leaflet quantity.*—Average of 12 per stem.

*Leaflet shape.*—Cordate.

*Leaflet base.*—Acute.

*Leaflet apex.*—Acuminate.

*Leaflet venation.*—Pinnate, color of upper surface; N144A, color of lower surface; 144C, sparsely covered with short strigose hairs 1 mm in length and 157A in color.

*Leaflet margins.*—Biserrate.

*Leaflet size.*—Average of 4.1 cm in length and 5 cm in width.

*Leaflet surface.*—Upper and lower surfaces moderately glossy and sparsely covered with short strigose hairs an average of 0.5 mm in length and 157C in color.

*Leaflet color.*—Emerging foliage upper and lower surface; a blend of 10A and 18A, young foliage upper and lower surface; a color between 4A and 150A, summer foliage upper and lower foliage; a blend of 145A and 150A with a blush of 192A after flowering.

*Petioles.*—Leaf; up to 11 cm in length, 2 mm in diameter and 145C mixed with 200A in color, glabrous surface, very sparsely covered with short strigose hairs 1 mm in length and matches petiole color, petiolules; average of 1 cm in length, 2 mm in diameter blend of 175A and 177A in color, glabrous surface, very sparsely covered with short strigose hairs 1 mm in length and matches petiolules color.

Flower description:

*Inflorescence type.*—Numerous flowers arranged on pyramidal panicles.

*Inflorescence aspect.*—Upright and held above foliage.

*Inflorescence size.*—Average of 39.6 cm in height and 12.5 cm in width.

*Flower fragrance.*—Moderately strong, sweet and pleasant fragrance.

*Flower quantity.*—Average of 1,440 per inflorescence.

*Flower lastingness.*—Average of 10 days.

*Flower buds.*—Broadly ovate in shape, average of 2.5 mm in length and 1.75 mm in diameter, color; 63B with base 145A.

*Flower aspect.*—Upright and outward.

*Flower shape.*—Rotate.

*Flower size.*—An average 5 mm in depth and 7 mm in diameter.

*Petals.*—Average of 5, un-fused, oblanceolate in shape, margin is entire, apex is broad acute, upper and lower surface dull, average of 3 mm in length and width, color of upper and lower surface opening; a blend of 63B and 63C, color of upper and lower surface mature; a blend of 62A and 62B.

*Calyx.*—Campanulate, average of 2 mm in length and diameter.

*Sepals.*—5, ovate in shape, margin is entire, apex is acute, base is truncate and fused, surface is smooth and dull, color of upper and lower surface when immature; 145B to 145D, color of upper and lower surface when mature; 145B, an average of 1 mm in width and 2 mm in length.

*Bracts.*—1 to 2, at base of secondary racemes, lanceolate in shape, 144A in color, about 1 mm in width and 3 mm in length, attenuate apex, base truncate and fused to rachis, upper and lower surface glabrous.

*Peduncles.*—Average of 40 cm in length and 4 mm in diameter, held at an average angle of 15° to vertical, peduncles of secondary racemes; held at an average angle of 45°, an average of 6.5 cm in length and 1.5 mm in width, strong, color is a blend of 146C and 166A to 166B, glabrous surface.

*Pedicels.*—About 1 mm in length and 0.5 mm in width, held at an average angle of 30°, color is a blend of 146C and 166A to 166B, glabrous surface.

Reproductive organs:

*Gynoecium.*—2 Pistils, about 2.5 mm in length, stigma is club-shaped and 69B in color, style is about 1 mm in length and 64B in color, ovary is 155A in color.

*Androcoecium.*—An average of 10 stamens, anthers are ovate in shape, basifixed, about 0.2 mm in length and 161D in color, filaments are about 2 mm in length and N155C in color, pollen is very low in quantity and N155A in color.

*Seed and fruit.*—No seeds or fruit have been detected to date.

It is claimed:

1. A new and distinct cultivar of *Astilbe* plant named 'Amber Moon' as herein illustrated and described.

* * * * *